United States Patent
Huang et al.

(10) Patent No.: US 6,761,707 B2
(45) Date of Patent: Jul. 13, 2004

(54) SAFETY SYRINGE HAVING NEEDLE HOLDER CAPABLE OF FIXING SECURED AND EASY TO DRAWBACK

(75) Inventors: Chin-Shu Huang, Hsinchu (TW); Tzu-Sheng Fan, Miao Li Hsien (TW); Chien-Wei Chung, Taichung (TW)

(73) Assignee: Taiject Medical Device Co., Ltd., Miaoli (TW)

( * ) Notice: Subject to any disclaimer, the term of this patent is extended or adjusted under 35 U.S.C. 154(b) by 89 days.

(21) Appl. No.: 10/141,173

(22) Filed: May 9, 2002

(65) Prior Publication Data

US 2003/0153878 A1 Aug. 14, 2003

(30) Foreign Application Priority Data

Feb. 8, 2002 (TW) .................................. 91201650 U

(51) Int. Cl.⁷ .................................................. A61M 5/00
(52) U.S. Cl. ....................... 604/240; 604/110; 604/222; 604/228; 604/229
(58) Field of Search .............................. 604/110, 93.01, 604/240, 241, 242, 243, 181, 187, 218, 222, 225, 228, 229

(56) References Cited

U.S. PATENT DOCUMENTS

| | | | | |
|---|---|---|---|---|
| 5,047,016 A | * | 9/1991 | Dolgin et al. ............... | 604/110 |
| 5,049,133 A | * | 9/1991 | Villen Pascual ............ | 604/110 |
| 5,188,599 A | * | 2/1993 | Botich et al. ............... | 604/110 |
| 5,211,628 A | * | 5/1993 | Marshall ..................... | 604/110 |
| 5,578,015 A | * | 11/1996 | Robb ......................... | 604/195 |
| 5,782,804 A | * | 7/1998 | McMahon ................... | 604/110 |
| 5,976,108 A | * | 11/1999 | Liu ............................ | 604/110 |
| 6,342,045 B1 | * | 1/2002 | Somers ...................... | 604/110 |
| 6,391,008 B1 | * | 5/2002 | Tsai ........................... | 604/195 |
| 6,494,863 B1 | * | 12/2002 | Shaw et al. ................. | 604/110 |
| 6,558,357 B1 | * | 5/2003 | Hoeck ........................ | 604/195 |
| 2002/0077602 A1 | * | 6/2002 | Hsu ........................... | 604/240 |
| 2002/0183699 A1 | * | 12/2002 | Targell ....................... | 604/243 |
| 2003/0028151 A1 | * | 2/2003 | Righi et al. ................. | 604/218 |
| 2003/0050601 A1 | * | 3/2003 | Righi et al. ................. | 604/110 |
| 2003/0083627 A1 | * | 5/2003 | Chen .......................... | 604/240 |
| 2003/0093038 A1 | * | 5/2003 | Chiang ....................... | 604/240 |

* cited by examiner

Primary Examiner—Brian L. Casler
Assistant Examiner—Jeremy Thissell
(74) Attorney, Agent, or Firm—Browdy and Neimark, P.L.L.C.

(57) ABSTRACT

A safety syringe comprises a barrel, which has a body forming a receiving hole, a stop portion in the receiving hole. A needle holder has a hole therein, an elastic lock piece formed a claw at distal end, and a dragged portion. The needle holder is received in the receiving hole of the barrel for the claw can lock with the stop portion of the barrel. A supporter, which is slidable received in the hole of the needle holder for supporting the elastic lock pieces to make the needle holder fixed secured in the barrel. And a plunger set has a bumper to move away said supporter and withdraw said needle holder.

9 Claims, 7 Drawing Sheets

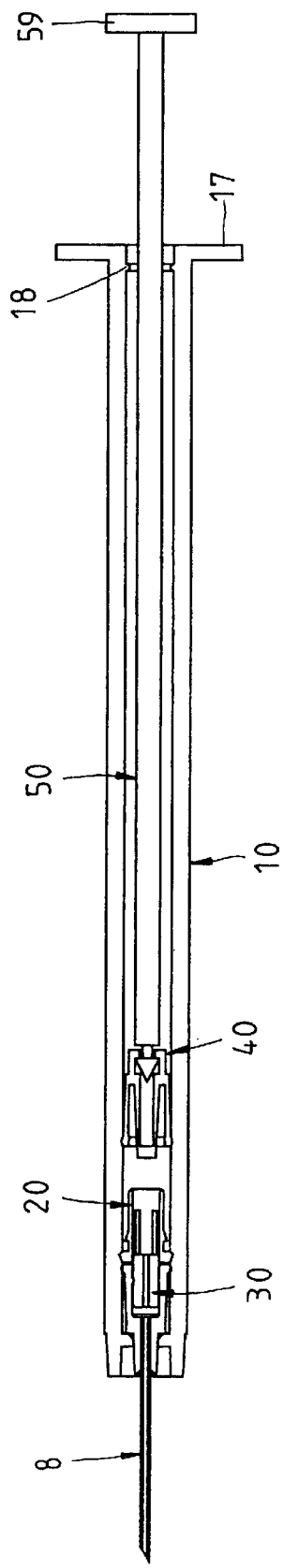
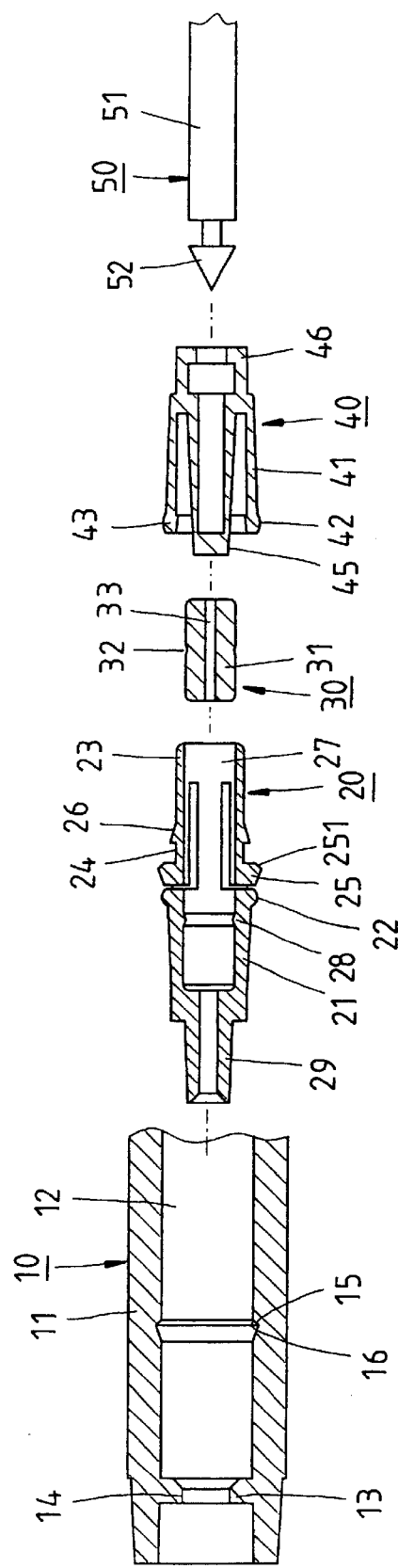
FIG. 2
FIG. 3

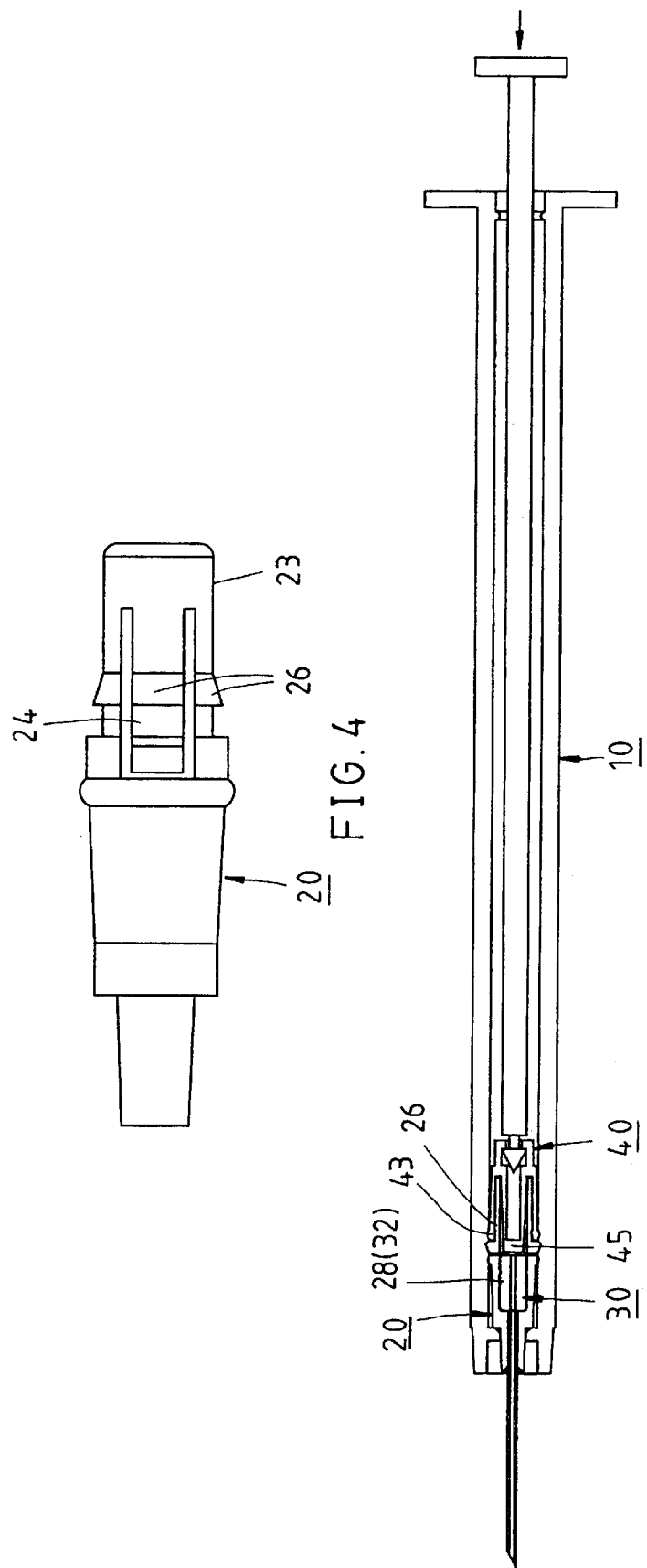

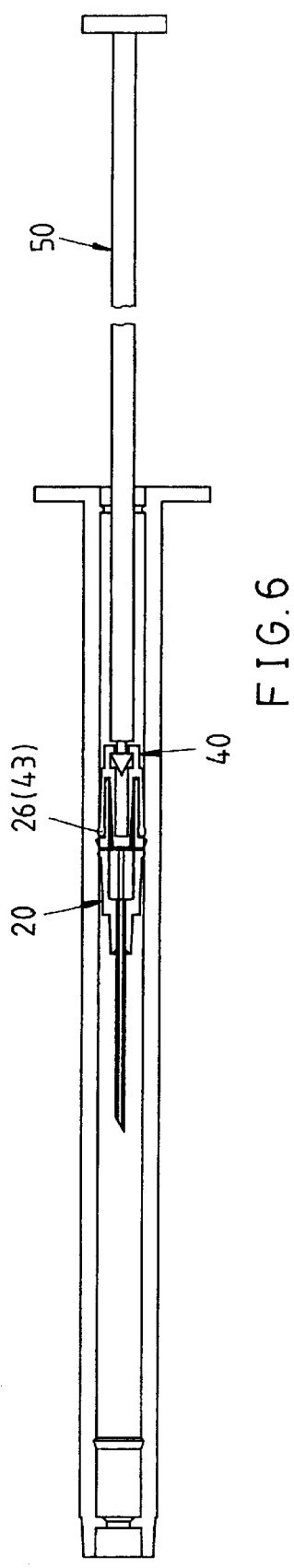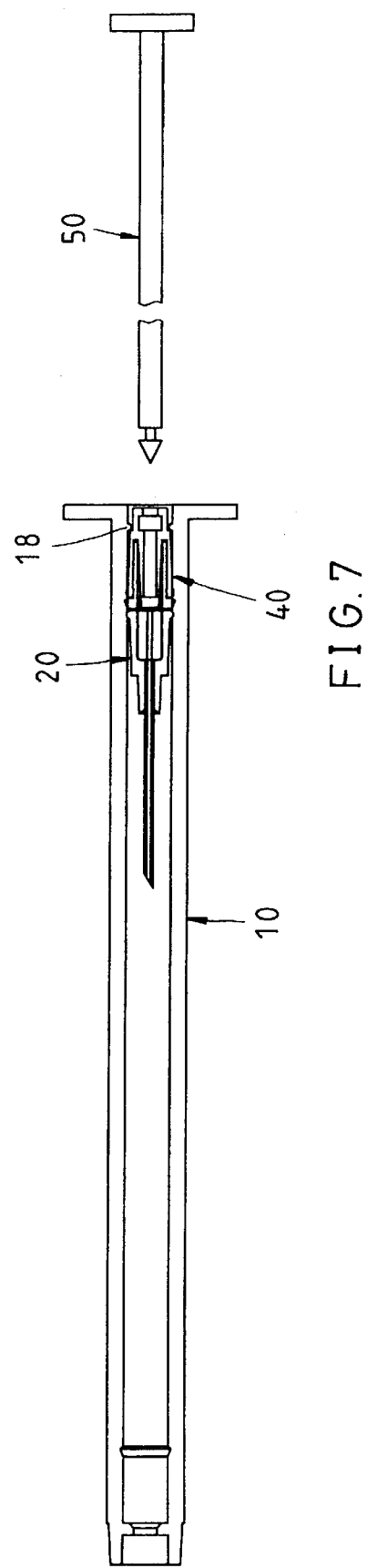

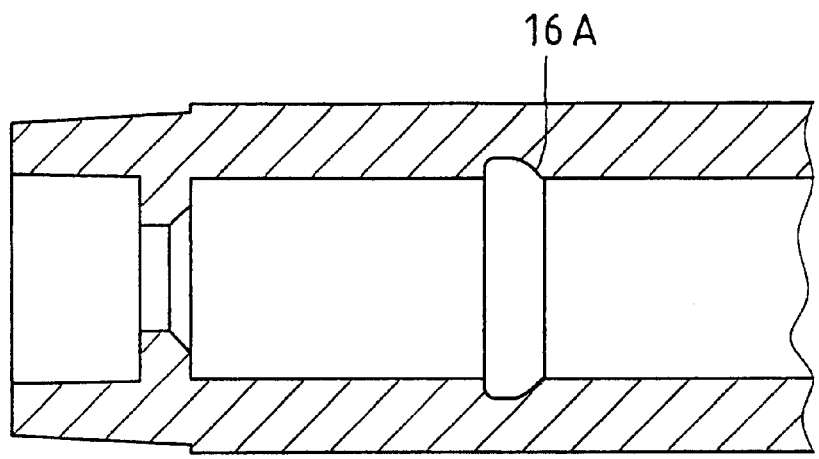
(a)
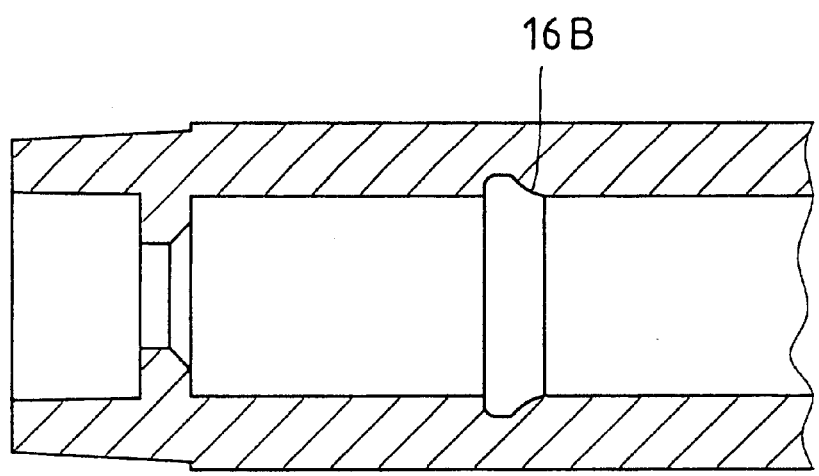
(b)
FIG. 8

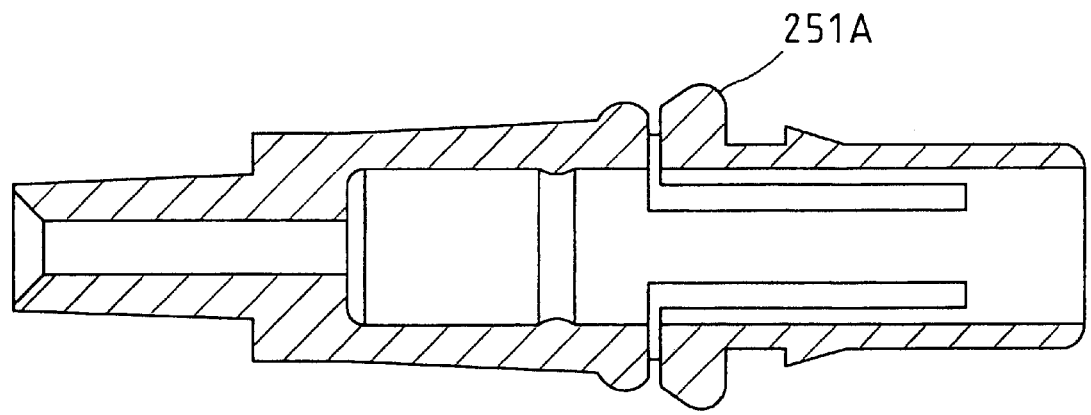
(a)
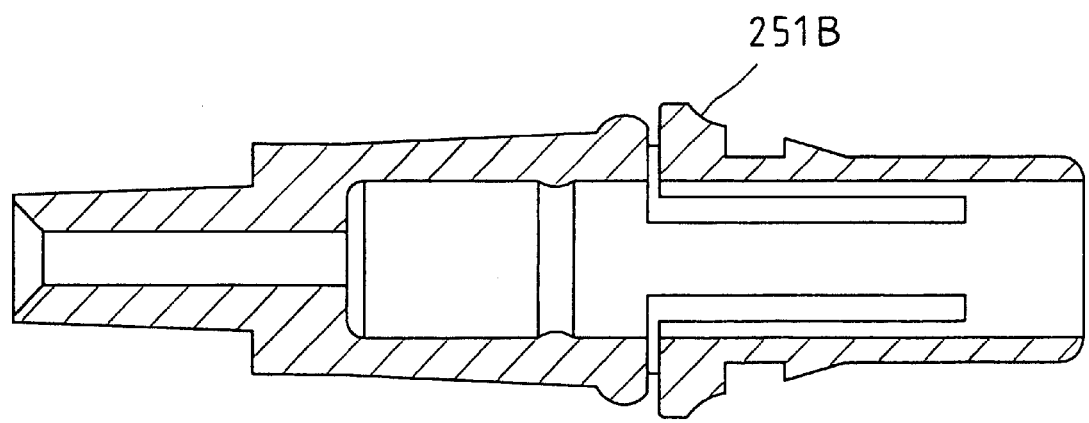
(b)
FIG. 9

SAFETY SYRINGE HAVING NEEDLE HOLDER CAPABLE OF FIXING SECURED AND EASY TO DRAWBACK

FIELD OF THE INVENTION

The present invention relates to a hypodermic syringe, and more particularly to a safety syringe, which is easy to draw the needle back after injection but the needle holder is fixed secured in the barrel when injecting.

BACKGROUND OF THE INVENTION

A conventional safety syringe, which can draw the needle into the barrel, usually provides the needle holder a little position force for the needle holder is easy to run back into the barrel while an external force is exerted on the needle holder.

There were many inventions to fix the problem as described above, such as provides double locking devices to secure the needle holder. These inventions usually have complex structure and sometime they can not work correctly.

SUMMARY OF THE INVENTION

The primary object of the present invention is to provide a safety syringe, which can fixed secure the needle holder in the barrel.

Another objective of the present invention is to provide a safety syringe, which is easy to draw the needle holder into the barrel.

According to the objective of the present invention, a safety syringe comprises a barrel, which has a body, a receiving hole in the body, a front opening at an end of the body and a stop portion in the receiving hole. A needle holder has a hole therein, an elastic lock piece has a claw at distal end, and a dragged portion. The needle holder is to mount a needle. The needle holder is received in the receiving hole of the barrel for the claw can lock with the stop portion in the receiving hole. A supporter, which has a aperture, is slidable received in the hole of the needle holder. And a plunger set has a bumper to move away the supporter and withdraw the needle holder.

For better use, the plunger set may comprises a plunger and a stopper.

BRIEF DESCRIPTION OF THE DRAWINGS

FIG. 2 is a sectional view of the prefer embodiment of the present invention in combination;

FIG. 3 is an exploded view of the safety syringe shown in FIG. 2;

FIG. 4 is a top view of the needle holder of a prefer embodiment of the present invention;

FIG. 5 is a sectional view of the prefer embodiment of the present invention, showing the stopper locking with the needle holder;

FIG. 6 is a sectional view of the prefer embodiment of the present invention, showing the needle holder being drawn back into barrel;

FIG. 7 is a sectional view of the prefer embodiment of the present invention following FIG. 6, showing the plunger being separated;

FIG. 8a and FIG. 8b are sectional views of the prefer embodiment of the present invention, showing the alternations of the sliding face in barrel;

FIG. 9a and FIG. 9b are sectional views of the prefer embodiment of the present invention, showing the alternations of the sliding face in needle holder;

DETAIL DESCRIPTION OF THE INVENTION

Figure 1:
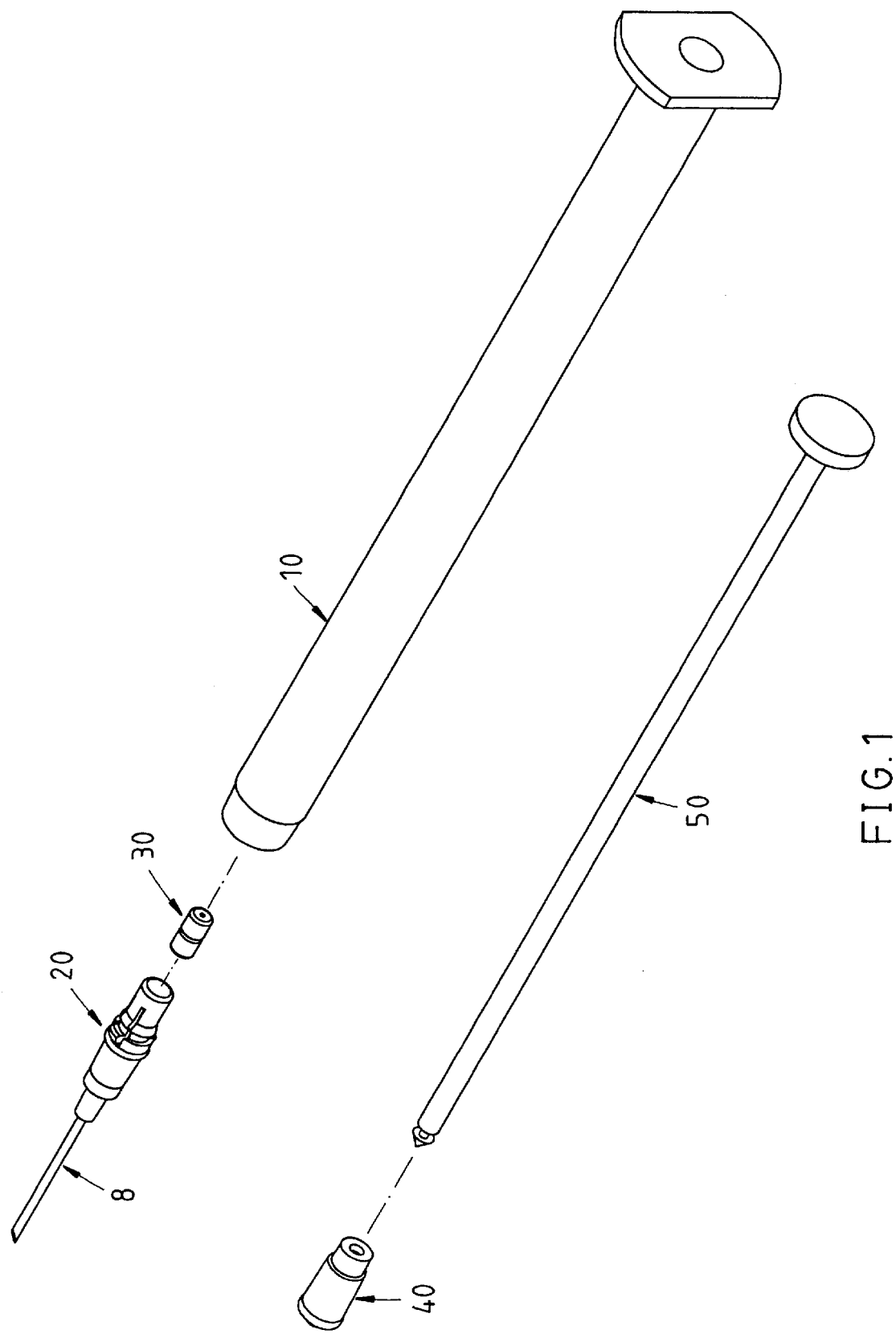
FIG. 1 is an exploded view of a prefer embodiment of the present invention.

Please refer to FIGS. 1–4, a safety syringe of the prefer embodiment of the present invention, which is to mount a needle 8, comprises:

A barrel 10 has a body 11, which has a receiving hole 12 therein. The body 11 has a stop flange 13 at front end of the receiving hole 12. A front opening 14 is formed at central of the stop flange 13. A stop portion 15 formed cone-shaped is disposed in the receiving hole 12 behind the stop flange 13, which has a sliding face 16 on the sidewall of the receiving hole 12. A hold portion 17 at rear end of the body 11, and a retaining portion 18 in rear side of the receiving hole 12.

A needle holder 20 has an engage portion 21 and a seal ring 22 at rear end thereof, an extend tube 23 at rear end of the engage portion 21, a needle receiver 29 at front end of the engage portion 21 for fit the needle 8, a hole 27 passing through the extend tube 23 and the engage portion 21. The engage portion 21 has. The extend tube 23 has two elastic lock pieces 24 thereon, each of which has a claw 25 at distal end thereof, and a dragged portion 26 at exterior side thereof. Each claw 25 has a sliding face 251 thereon. The hole 27 has a locating ring 28 on the interior sidewall thereof.

The needle holder 20 is received in the receiving hole 12 of the barrel 10. The seal ring 22 is against the sidewall of the receiving hole 12 to provide watertight capacity. The claws 25 are locked by the stop portion 15 to position the needle holder 20 in the receiving hole 12 of the barrel 10.

A supporter 30 has a body 31, a position slot 32 at exterior side of the body 31 and a tunnel 33 passing through the body 31. The supporter 30 is received in the 31 hole 27 of the needle holder 20 in slight interference fit. But the supporter 30 still can be driven to slide in the hole 27. In initial, the supporter 30 supports the elastic lock pieces 24 of the needle holder 20 to make the claws 25 can not escape from the stop portion 15 of the barrel 10. Thus, the needle holder 20 is fixed secured in the receiving hole 12 of the barrel 10.

A stopper 40 has a body 41, which is opening at front end. The body 41 has a seal ring 42 at exterior side, a drag portion 43 at interior side, a bumper 45 at central extending out of the opening end and a plunger connector 46 at rear end. The stopper 40 is received in the receiving hole 12 of the barrel 10 with the seal ring 42 being against the sidewall of the receiving hole 12 to provide watertight capacity. The stopper 40 can slide in the receiving hole 12.

A plunger 50 has a shank 51, which has a stopper connector 52 at an end thereof and a push-pull portion 59 at the other end thereof. The plunger 50 is inserted into the receiving hole 12 of the barrel 10 with the stopper connector 52 buckling the plunger connector 46 of the stopper 40.

In assembly, put the supporter 30 inside the receiving hole 12 of the needle holder 20, then put the needle holder 20 into the receiving hole 12 of the barrel 10, and let the claws 25 of the needle holder 20 fit to the sliding face 16 of the barrel 10.

Then, insert the stopper 40 and plunger 50 into the receiving hole 12 of the barrel 10 in order, an let the stopper connector 52 buckling the plunger connector 46 of the stopper 40.

In use, please refer to FIG. 2, liquid drug (not shown) can be received in the receiving hole 12 of the barrel 10 between the stopper 40 and the needle holder 20.

FIG. 5 shows the safety syringe had injected drug. The supporter 30 is pushed by the bumper 45 of the stopper 40 to slide more inside of the hole 27 of the needle holder 20, the elastic lock pieces 24 of the needle holder 20 are no longer support by the supporter 30 anymore, and the drag portion 43 of the stopper 40 catch the dragged portion 26 of the needle holder 20.

Please refer to FIG. 6, when withdraw the plunger 50 with the stopper 40, the needle holder 20 can be moved for the sliding face 251 of the claw 25 being slide with the sliding face 16 of the barrel 10, and the elastic lock pieces 24 of the needle holder 20 bent inward, so the needle holder 20 can be moved along with the stopper 40 easily.

As shown in FIG. 7, the stopper 40 will be stopped by the retaining portion 18 of said barrel 10, user may exert a larger force on the plunger 50 to make the plunger 50 departing from the stopper 40.

In addition, the stopper and the plunger can be made as a unit (not shown), and the plunger can be broken after being pulled back.

FIG. 8*a* and FIG. 8*b* show two alternations of the sliding faces 16A and 16B of the barrel has curved face outwards and inwards. It is same, FIG. 9*a* and FIG. 9*b* show two alternations of the sliding faces 251A and 251B of the needle holder has curved face outwards and inwards.

Figure 10:
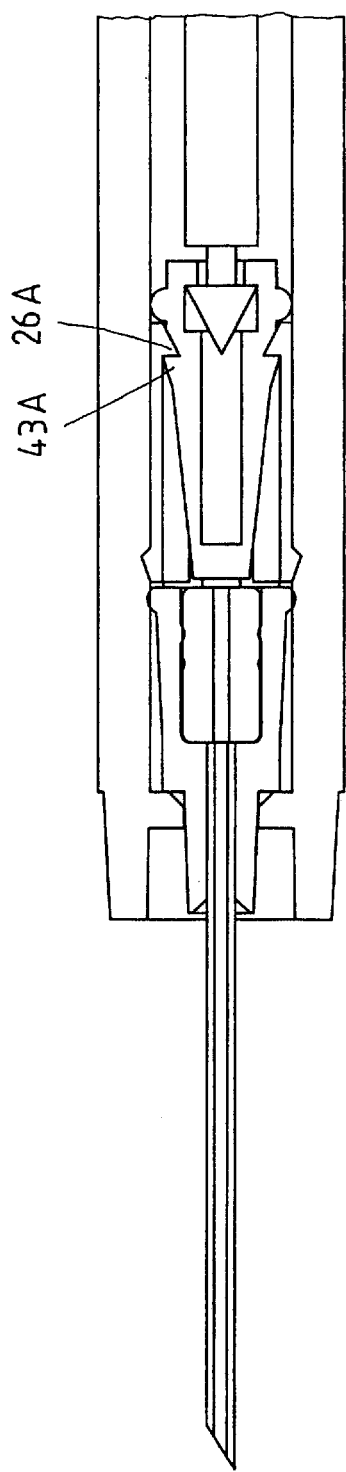
FIG. 10 is a sectional view of the prefer embodiment of the present invention, showing an alternation of the plunger with the needle holder.

FIG. 10 shows an alternation of the dragged portion 26A, which is a hook-like element located at the sidewall of the hole of the needle holder, and the drag portion 43A, which a hook-like element at exterior side of the stopper.

Figure 11:
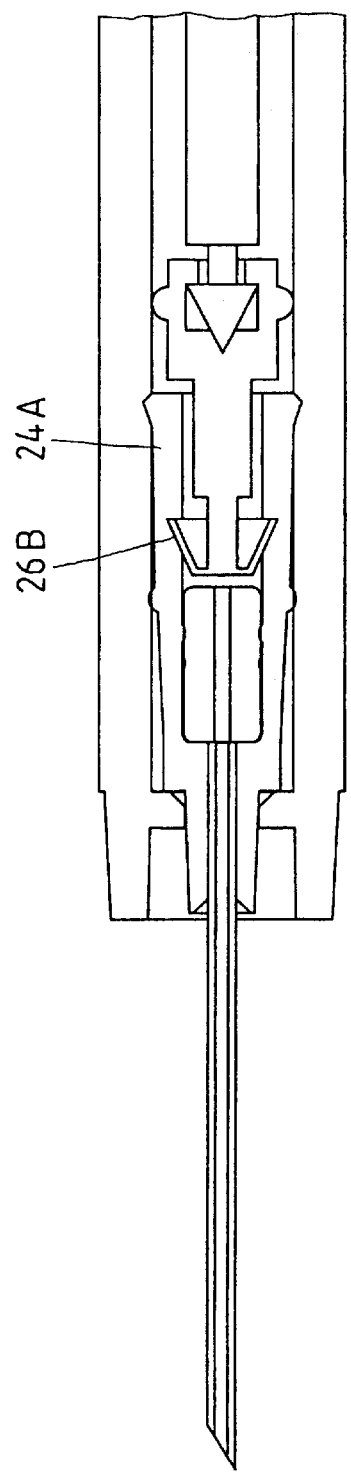
FIG. 11 is a sectional view of the prefer embodiment of the present invention, showing another alternation of the plunger with the needle holder.

FIG. 11 shows an alternation of the elastic lock piece 24A, which extends to the rear end of the needle holder, and the dragged portion 26B is a slot around the sidewall of the hole of the needle holder.

By the description of embodiments above, the advantages of the present invention are:

1. The safety syringe of the present invention provides the supporter in the needle holder to make the needle holder being fixed secured in the barrel before injection.
2. The safety syringe of the present invention is easy to draw the needle holder back smoothly and power-save after injection.

What is claimed is:

1. A safety syringe, which is to mount a needle, comprising:
    a barrel having a body, a receiving hole in said body, a front opening at an end of said body and a stop portion in said receiving hole;
    a needle holder having a hole therein, an elastic lock piece having a claw at a distal end and a dragged portion; said needle holder being adapted to mount said needle thereon; said needle holder being received in said receiving hole of said barrel so said claw can lock with said stop portion in said receiving hole;
    a supporter slidably received in said hole of said needle holder and located inside and supporting the elastic lock piece of the needle holder, said supporter having an aperture; and
    a plunger set having a bumper to move away said supporter and withdraw said needle holder.

2. The safety syringe as defined in claim 1, wherein said stop portion of said barrel has a sliding face for sliding of said claw of said needle holder.

3. The safety syringe as defined in claim 2, wherein said sliding face of the barrel is a curved face.

4. The safety syringe as defined in claim 1, wherein said claw of said needle holder has a sliding face thereon for sliding of said stop portion of said barrel.

5. The safety syringe as defined in claim 4, wherein said sliding face of said claw of the needle holder is a curved face.

6. The safety syringe as defined in claim 1, wherein said plunger set comprises a stopper and a plunger.

7. The safety syringe as defined in claim 6, wherein said plunger has a stopper connector at the front end for pull a plunger connector of said stopper.

8. The safety syringe as defined in claim 6, wherein said stopper has a seal ring at exterior thereof for sealing said receiving hole of the barrel.

9. A safety syringe, which is to mount a needle, comprising:
    a barrel having a body, a receiving hole in said body, a front opening at an end of said body and a stop portion in said receiving hole;
    a needle holder having a hole therein, an elastic lock piece having a claw at a distal end and a dragged portion; said needle holder being adapted to mount said needle thereon; said needle holder being received in said receiving hole of said barrel so said claw can lock with said stop portion in said receiving hole;
    a supporter slidably received in said hole of said needle holder and located inside and supporting the elastic lock piece of the needle holder, said supporter having an aperture;
    a plunger set having a bumper to move away said supporter and withdraw said needle holder;
    wherein set plunger set comprises a stopper and a plunger;
    wherein said stopper has a drag portion set inwards to drag said dragged portion of the needle holder.

\* \* \* \* \*